(12) United States Patent
Nicholas et al.

(10) Patent No.: US 11,871,924 B2
(45) Date of Patent: Jan. 16, 2024

(54) HAND-HELD SURGICAL INSTRUMENTS

(71) Applicant: Covidien LP, Mansfield, MA (US)

(72) Inventors: David A Nicholas, Trumbull, CT (US); Russell V. Pribanic, Roxbury, CT (US)

(73) Assignee: COVIDIEN LP, Mansfield, MA (US)

( * ) Notice: Subject to any disclaimer, the term of this patent is extended or adjusted under 35 U.S.C. 154(b) by 689 days.

(21) Appl. No.: 17/090,093

(22) Filed: Nov. 5, 2020

(65) Prior Publication Data

US 2021/0068823 A1    Mar. 11, 2021

Related U.S. Application Data

(63) Continuation-in-part of application No. 17/089,827, filed on Nov. 5, 2020, now Pat. No. 11,510,669, and
(Continued)

(51) Int. Cl.
    *A61B 17/068*      (2006.01)
    *A61B 17/072*      (2006.01)
    (Continued)

(52) U.S. Cl.
    CPC ........ *A61B 17/0686* (2013.01); *A61B 17/072* (2013.01); *A61B 17/068* (2013.01); *A61B 17/07207* (2013.01); *A61B 17/10* (2013.01); *A61B 17/1155* (2013.01); *A61B 2017/00398* (2013.01); *A61B 2017/00734* (2013.01);
(Continued)

(58) Field of Classification Search
CPC ............... A61B 17/068; A61B 17/072; A61B 17/07207; A61B 17/105; A61B 17/10; A61B 2017/00017; A61B 2017/00119; A61B 2017/00398; A61B 2017/00734; A61B 2017/07214; A61B 2017/2923; A61B 2017/2927; A61B 34/30; A61B 34/70; A61B 34/71; A61B 90/98
USPC ..... 227/19, 175.1, 175.2, 176.1; 606/1, 139, 606/219
See application file for complete search history.

(56) References Cited

U.S. PATENT DOCUMENTS

| 4,196,348 A | 4/1980 | Iwakiri et al. |
| 4,803,362 A | 2/1989 | Butts |

(Continued)

FOREIGN PATENT DOCUMENTS

| CA | 3073178 A1 | 2/2019 |
| CN | 101227187 A | 7/2008 |

(Continued)

OTHER PUBLICATIONS

European Search Report dated Sep. 15, 2021, issued in corresponding EP Appln. No. 20211924, 10 pages.

*Primary Examiner* — Scott A Smith
(74) *Attorney, Agent, or Firm* — Carter, DeLuca & Farrell, LLP (57) ABSTRACT

A surgical instrument module for powering a plurality of discrete surgical end effectors includes a motor, a planetary gear box, a high-torque/low-speed output operably coupled to the motor, and a high-speed/low-torque output operably coupled to the motor. The high-torque/low-speed is configured to be operably coupled to a driven member of a first type of surgical end effector, and the high-speed/low-torque output is configured to drive an operation of a second type of surgical end effector.

20 Claims, 7 Drawing Sheets

Related U.S. Application Data a continuation-in-part of application No. 17/089,870, filed on Nov. 5, 2020, now Pat. No. 11,389,159, and a continuation-in-part of application No. 17/089,813, filed on Nov. 5, 2020, now abandoned, and a continuation-in-part of application No. 17/089,789, filed on Nov. 5, 2020, now Pat. No. 11,395,655, said application No. 17/089,870 is a continuation-in-part of application No. 16/532,534, filed on Aug. 6, 2019, now Pat. No. 11,234,701.

(60) Provisional application No. 63/087,501, filed on Oct. 5, 2020, provisional application No. 63/084,656, filed on Sep. 29, 2020, provisional application No. 63/064,977, filed on Aug. 13, 2020, provisional application No. 62/944,400, filed on Dec. 6, 2019, provisional application No. 62/944,548, filed on Dec. 6, 2019, provisional application No. 62/734,290, filed on Sep. 21, 2018.

(51) Int. Cl.
*A61B 17/00* (2006.01)
*A61B 17/29* (2006.01)
*A61B 17/115* (2006.01)
*A61B 17/10* (2006.01)

(52) U.S. Cl.
CPC .............. *A61B 2017/07214* (2013.01); *A61B 2017/2923* (2013.01)

(56) References Cited

U.S. PATENT DOCUMENTS

| | | | |
|---|---|---|---|
| 5,321,311 A | 6/1994 | Umemura et al. | |
| 5,747,953 A | 5/1998 | Philipp | |
| 6,013,991 A | 1/2000 | Philipp | |
| 6,025,683 A | 2/2000 | Philipp | |
| 6,517,565 B1 | 2/2003 | Whitman et al. | |
| 6,960,894 B2 | 11/2005 | Carusillo et al. | |
| 7,638,958 B2 | 12/2009 | Philipp et al. | |
| 7,819,896 B2 | 10/2010 | Racenet | |
| 7,914,543 B2 | 3/2011 | Roth et al. | |
| 8,480,703 B2 | 7/2013 | Nicholas et al. | |
| 8,968,276 B2 | 3/2015 | Zemlok et al. | |
| 9,283,054 B2 | 3/2016 | Morgan et al. | |
| 9,307,986 B2 | 4/2016 | Hall et al. | |
| 9,326,767 B2 | 5/2016 | Koch, Jr. et al. | |
| 9,358,003 B2 | 6/2016 | Hall et al. | |
| 9,398,911 B2 | 7/2016 | Auld | |
| 9,468,438 B2 | 10/2016 | Baber et al. | |
| 9,554,794 B2 | 1/2017 | Baber | |
| 9,597,104 B2 | 3/2017 | Nicholas et al. | |
| 9,654,050 B2 | 5/2017 | Kokinelis | |
| 9,700,309 B2 | 7/2017 | Jaworek | |
| 9,700,318 B2 | 7/2017 | Scirica et al. | |
| 9,775,610 B2 | 10/2017 | Nicholas et al. | |
| 9,782,169 B2 | 10/2017 | Kimsey | |
| 9,782,187 B2 | 10/2017 | Zergiebel | |
| 9,801,646 B2 | 10/2017 | Zergiebel | |
| 9,991,069 B2 | 6/2018 | Nicholas et al. | |
| 10,441,281 B2 | 10/2019 | Shelton, IV et al. | |
| 11,389,159 B2 * | 7/2022 | Nicholas | A61B 17/068 |
| 11,395,655 B2 * | 7/2022 | Nicholas | A61B 17/072 |
| 11,510,669 B2 * | 11/2022 | Nicholas | A61B 17/068 |
| 2009/0095790 A1 | 4/2009 | Whitman et al. | |
| 2009/0108048 A1 | 4/2009 | Zemlok et al. | |
| 2009/0248041 A1 | 10/2009 | Williams et al. | |
| 2009/0283568 A1 | 11/2009 | Racenet et al. | |
| 2009/0314821 A1 | 12/2009 | Racenet | |
| 2010/0171026 A1 | 7/2010 | Saitou et al. | |
| 2010/0213240 A1 | 8/2010 | Kostrzewski | |
| 2011/0017801 A1 | 1/2011 | Zemlok et al. | |
| 2011/0121049 A1 | 5/2011 | Malinouskas et al. | |
| 2011/0204119 A1 | 8/2011 | McCuen | |
| 2012/0012638 A1 | 1/2012 | Huang | |
| 2012/0089131 A1 | 4/2012 | Zemlok et al. | |
| 2012/0130420 A1 | 5/2012 | Nicholas | |
| 2012/0253329 A1 | 10/2012 | Zemlok et al. | |
| 2012/0296159 A1 | 11/2012 | Kanazawa et al. | |
| 2012/0296316 A1 | 11/2012 | Imuta | |
| 2012/0303002 A1 | 11/2012 | Chowaniec et al. | |
| 2013/0184730 A1 | 7/2013 | Beardsley et al. | |
| 2013/0319706 A1 | 12/2013 | Nicholas et al. | |
| 2013/0324979 A1 | 12/2013 | Nicholas et al. | |
| 2014/0012238 A1 | 1/2014 | Chen et al. | |
| 2014/0114403 A1 | 4/2014 | Dale et al. | |
| 2014/0246477 A1 | 9/2014 | Koch, Jr. et al. | |
| 2014/0246479 A1 | 9/2014 | Baber et al. | |
| 2014/0249557 A1 | 9/2014 | Koch, Jr. et al. | |
| 2014/0299647 A1 | 10/2014 | Scirica et al. | |
| 2014/0303668 A1 | 10/2014 | Nicholas et al. | |
| 2014/0305987 A1 | 10/2014 | Parihar | |
| 2014/0309666 A1 * | 10/2014 | Shelton, IV | A61B 17/0686 606/139 |
| 2014/0358129 A1 | 12/2014 | Zergiebel et al. | |
| 2015/0005788 A1 | 1/2015 | Sniffin et al. | |
| 2015/0196295 A1 * | 7/2015 | Shelton, IV | A61B 34/30 227/175.1 |
| 2015/0235789 A1 | 8/2015 | Calderoni | |
| 2015/0374372 A1 | 12/2015 | Zergiebel et al. | |
| 2016/0066916 A1 | 3/2016 | Overmyer et al. | |
| 2016/0100838 A1 | 4/2016 | Beaupre et al. | |
| 2016/0166255 A1 * | 6/2016 | Fischvogt | A61B 17/068 606/139 |
| 2016/0324514 A1 | 11/2016 | Srinivas et al. | |
| 2017/0211667 A1 * | 7/2017 | Nicholas | A61B 34/71 |
| 2017/0224333 A1 | 8/2017 | Hunter et al. | |
| 2017/0245854 A1 | 8/2017 | Zemlok et al. | |
| 2018/0049738 A1 * | 2/2018 | Meloul | A61B 17/068 |
| 2019/0000475 A1 | 1/2019 | Shelton, IV et al. | |
| 2019/0261984 A1 | 8/2019 | Nelson et al. | |
| 2020/0093492 A1 * | 3/2020 | Pribanic | A61B 90/08 |

FOREIGN PATENT DOCUMENTS

| | | |
|---|---|---|
| CN | 203014768 U | 6/2013 |
| EP | 2055243 A2 | 5/2009 |
| EP | 2455007 A2 | 5/2012 |
| EP | 2676615 A2 | 12/2013 |
| EP | 2777539 A2 | 9/2014 |
| EP | 3011910 A1 | 4/2016 |
| GB | 2574099 A | 11/2019 |
| KR | 20020020332 A | 3/2002 |
| KR | 20070000199 U | 2/2007 |
| WO | 2008147415 A1 | 12/2008 |
| WO | 2017123837 A2 | 7/2017 |

\* cited by examiner

HAND-HELD SURGICAL INSTRUMENTS

CROSS-REFERENCE TO RELATED APPLICATIONS

The present application claims the benefit of and priority to U.S. Provisional Patent Application Ser. No. 63/064,977, filed on Aug. 13, 2020, the entire content of which being hereby incorporated by reference.

The present application is a Continuation-in-Part Application claiming the benefit of and priority to U.S. patent application Ser. No. 17/089,870, filed on Nov. 5, 2020, now U.S. Pat. No. 11,389,159, which is a Continuation-in-Part Application claiming the benefit of and priority to U.S. patent application Ser. No. 16/532,534, filed on Aug. 6, 2019, now U.S. Pat. No. 11,234,701, which claims the benefit of and priority to U.S. Provisional Patent Application No. 62/734,290, filed on Sep. 21, 2018, the entire disclosure of which is incorporated by reference herein.

U.S. patent application Ser. No. 17/089,870, also claims the benefit of and priority to U.S. Provisional Patent Application Ser. No. 63/087,501, filed on Oct. 5, 2020, the entire content of which being hereby incorporated by reference.

The present application is a Continuation-in-Part Application claiming the benefit of and priority to U.S. patent application Ser. No. 17/089,827, filed on Nov. 5, 2020, now U.S. Pat. No. 11,510,669, which claims the benefit of and priority to U.S. Provisional Patent Application Ser. No. 63/084,656, filed on Sep. 29, 2020, the entire content of which being hereby incorporated by reference.

The present application is a Continuation-in-Part Application claiming the benefit of and priority to U.S. patent application Ser. No. 17/089,813, filed on Nov. 5, 2020, now abandoned, which claims the benefit of and priority to U.S. Provisional Patent Application Ser. No. 62/944,548, filed on Dec. 6, 2019, the entire content of which being hereby incorporated by reference.

The present application is a Continuation-in-Part Application claiming the benefit of and priority to U.S. patent application Ser. No. 17/089,789, filed on Nov. 5, 2020, now U.S. Pat. No. 11,395,655, which claims the benefit of and priority to U.S. Provisional Patent Application Ser. No. 62/944,400, filed on Dec. 6, 2019, the entire content of which being hereby incorporated by reference.

BACKGROUND

A number of handle assembly manufacturers have developed product lines with proprietary drive systems for operating and/or manipulating electromechanical surgical instruments. In many instances the electromechanical surgical instruments include a handle assembly, which is reusable, and disposable loading units and/or single use loading units, such as, for example, surgical end effectors that are selectively connected to the handle assembly prior to use and then disconnected from the handle assembly following use in order to be disposed of or in some instances sterilized for re-use.

SUMMARY

In one aspect of the present disclosure, a surgical instrument module for powering surgical end effectors is provided. The surgical instrument module includes a motor having a rotatable motor shaft that defines a longitudinal axis, a main sun gear fixed to the motor shaft and configured to rotate with the motor shaft, first, second, third, and fourth planetary gear assemblies, a drive shaft, a high-torque output, and a high-speed output. The first planetary gear assembly is operably coupled to the main sun gear such that the first planetary gear assembly rotates about the longitudinal axis in response to a rotation of the main sun gear. The second planetary gear assembly is operably coupled to the first planetary gear assembly such that the second planetary gear assembly rotates in response to the rotation of the first planetary gear assembly. The drive shaft is non-rotatably coupled to the second planetary gear assembly such that the drive shaft rotates with the second planetary gear assembly. The third planetary gear assembly is operably coupled to the second planetary gear assembly such that the third planetary gear assembly rotates in response to the rotation of the second planetary gear assembly. The fourth planetary gear assembly is operably coupled to the third planetary gear assembly such that the fourth planetary gear assembly rotates in response to the rotation of the third planetary gear assembly. The high-torque output is configured to be operably coupled to a driven member of a first surgical end effector. The high-torque output gear is non-rotatably coupled to the fourth planetary gear assembly such that the high-torque output rotates with the fourth planetary gear assembly. The high-speed output is configured to be operably coupled to a driven member of a second surgical end effector. The high-speed output is non-rotatably coupled to the drive shaft such that the high-speed output rotates with the drive shaft.

In aspects, the high-speed output may be concentrically disposed within the high-torque output.

In aspects, the high-speed and high-torque outputs may be configured to rotate simultaneously in response to an activation of the motor.

In aspects, the high-torque output may include a pinion gear and the high-speed output may include a socket.

In aspects, the drive shaft may extend longitudinally through the third and fourth planetary gear assemblies.

In aspects, the drive shaft may have a proximal end portion fixed to the second planetary gear assembly, and a distal end portion disposed within and rotatable relative to the high-torque output.

In aspects, the high-torque output may define a cavity therein, and the high-speed output may be received in the cavity.

In aspects, the high-speed output may be configured to move longitudinally relative to and along the drive shaft.

In aspects, the surgical instrument module may further include a biasing member captured between the high-speed output and an inner surface of the high-torque output. The biasing member may be configured to distally-bias the high-speed output.

In aspects, the surgical instrument module may further include an elongate ring gear in meshing engagement with each of the planetary gear assemblies.

In aspects, each of the planetary gear assemblies may be disposed within the elongate ring gear.

In aspects, the elongate ring gear may be rotationally fixed relative to the motor.

In aspects, the first planetary gear assembly may include a first carrier, a plurality of planetary gears rotatably coupled to the first carrier and operably engaged with the main sun gear, and a first sun gear rotationally fixed to the first carrier.

In aspects, the second planetary gear assembly may include a second carrier, a plurality of planetary gears rotatably coupled to the second carrier and operably engaged with the first sun gear, and a second sun gear rotationally fixed to the second carrier.

In aspects, the drive shaft may have a proximal end portion disposed within and rotationally fixed to the second sun gear.

In aspects, the third planetary gear assembly may include a third carrier, a plurality of planetary gears rotatably coupled to the third carrier and operably engaged with the second sun gear, and a third sun gear rotationally fixed to the third carrier.

In aspects, the fourth planetary gear assembly may include a fourth carrier non-rotationally fixed to the high-torque output, and a plurality of planetary gears rotatably coupled to the fourth carrier and operably engaged with the third sun gear.

In aspects, the surgical instrument module may further include an elongate ring gear in meshing engagement with the plurality of planetary gears of each of the planetary gear assemblies.

In aspects, the surgical instrument module may further include an outer shell in which the elongate ring gear is received. The elongate ring gear may be non-rotatable relative to the outer shell.

In aspects, the surgical instrument module may further include a battery received in the outer shell and configured to power the motor, and a printed circuit board received in the outer shell and in communication with the battery and the motor.

In accordance with another aspect of the disclosure, a surgical instrument module for powering a plurality of discrete surgical end effectors is provided. The surgical instrument module includes a motor having a rotatable motor shaft that defines a longitudinal axis, a main sun gear fixed to the motor shaft and configured to rotate with the motor shaft, a first planetary gear assembly operably coupled to the main sun gear such that the first planetary gear assembly rotates about the longitudinal axis in response to a rotation of the main sun gear, a second planetary gear assembly operably coupled to the first planetary gear assembly such that the second planetary gear assembly rotates in response to the rotation of the first planetary gear assembly, a drive shaft having a proximal end portion non-rotatably coupled to the second planetary gear assembly, a high-torque output, and a high-speed output. The drive shaft is configured to rotate with the second planetary gear assembly. The high-torque output gear is operably coupled to the motor and configured to be operably coupled to a driven member of a first type of surgical end effector. The high-speed output is configured to drive an operation of a second type of surgical end effector. The high-speed output is non-rotatably coupled to a distal end portion of the drive shaft such that the high-speed output rotates with the drive shaft.

In aspects, the distal end portion of the drive shaft may be disposed within and rotatable relative to the high-torque output.

In aspects, the surgical instrument module may further include third and fourth planetary gear assemblies. The third planetary gear assembly may be operably coupled to the second planetary gear assembly such that the third planetary gear assembly rotates in response to the rotation of the second planetary gear assembly. The fourth planetary gear assembly may be operably coupled to the third planetary gear assembly such that the fourth planetary gear assembly rotates in response to the rotation of the third planetary gear assembly. The high-torque output may be non-rotatably coupled to the fourth planetary gear assembly such that the high-torque output rotates with the fourth planetary gear assembly.

In aspects, the drive shaft may extend longitudinally through the third and fourth planetary gear assemblies.

In aspects, the drive shaft may be rotatable relative to each of the third and fourth planetary gear assemblies.

In accordance with another aspect of the disclosure, a handle assembly of a hand-held surgical instrument is provided. The handle assembly includes a handle housing defining a cavity therein, and an instrument module configured for removable receipt in the cavity of the handle housing. The instrument module includes an outer shell, a motor having a rotatable motor shaft that defines a longitudinal axis, a battery received in the outer shell and configured to power the motor, a printed circuit board received in the outer shell and in communication with the battery and the motor, a main sun gear fixed to the motor shaft and configured to rotate with the motor shaft, first and second planetary gear assemblies, a drive shaft configured to rotate with the second planetary gear assembly, a high-torque output operably coupled to the motor, and a high-speed output. The first planetary gear assembly is operably coupled to the main sun gear such that the first planetary gear assembly rotates about the longitudinal axis in response to a rotation of the main sun gear. The second planetary gear assembly is operably coupled to the first planetary gear assembly such that the second planetary gear assembly rotates in response to the rotation of the first planetary gear assembly. The drive shaft has a proximal end portion non-rotatably coupled to the second planetary gear assembly. The high-speed output is non-rotatably coupled to a distal end portion of the drive shaft such that the high-speed output rotates with the drive shaft.

In aspects, the handle assembly may further include an elongate ring gear in meshing engagement with each of the planetary gear assemblies.

In aspects, each of the planetary gear assemblies may be disposed within the elongate ring gear.

In aspects, the elongate ring gear may be rotationally fixed relative to the outer shell.

In aspects, the handle assembly may further include third and fourth planetary gear assemblies. The third planetary gear assembly may be operably coupled to the second planetary gear assembly such that the third planetary gear assembly rotates in response to the rotation of the second planetary gear assembly. The fourth planetary gear assembly may be operably coupled to the third planetary gear assembly such that the fourth planetary gear assembly rotates in response to the rotation of the third planetary gear assembly. The high-torque output may be non-rotatably coupled to the fourth planetary gear assembly such that the high-torque output rotates with the fourth planetary gear assembly.

In aspects, the drive shaft may extend longitudinally through the third and fourth planetary gear assemblies.

In aspects, the drive shaft may be rotatable relative to each of the third and fourth planetary gear assemblies.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Embodiments of the present disclosure are described herein with reference to the accompanying drawings, wherein.

DETAILED DESCRIPTION

Embodiments of the presently disclosed surgical instruments including handle assemblies thereof are described in detail with reference to the drawings, in which like reference numerals designate identical or corresponding elements in each of the several views. As used herein the term "distal" refers to that portion of the surgical instrument, or component thereof, farther from the user, while the term "proximal" refers to that portion of the surgical instrument, or component thereof, closer to the user.

As will be described in detail below, provided is a surgical instrument module configured for receipt in a handle assembly of a plurality of discrete hand-held surgical instruments. The instrument module may be reusable and is configured to operate various functions of a plurality of different types of surgical end effectors, such as, for example, a linear stapler, a circular stapler, a hernia tacker, and a small-diameter vascular stapler. The surgical instrument module has two outputs with each operably coupled to the same motor of the surgical instrument module. A high-speed/low-torque output may be disposed concentrically within a high-torque/low-speed output. The outputs are rotated simultaneously by the motor, but each at a different speed and torque from the other. Depending on the surgical instrument in which the instrument module is received and operably engaged with, either the high-speed/low-torque output or the high-torque/low-speed output of the instrument module selectively engages a corresponding driven component (e.g., a rod, screw, rack, gear, or the like) of the selected surgical instrument. As such, the same instrument module may be used in a variety of surgical instruments despite each of the surgical instruments having discrete power and speed requirements. Other features and benefits of the disclosed surgical instruments are further detailed below.

Figure 1:
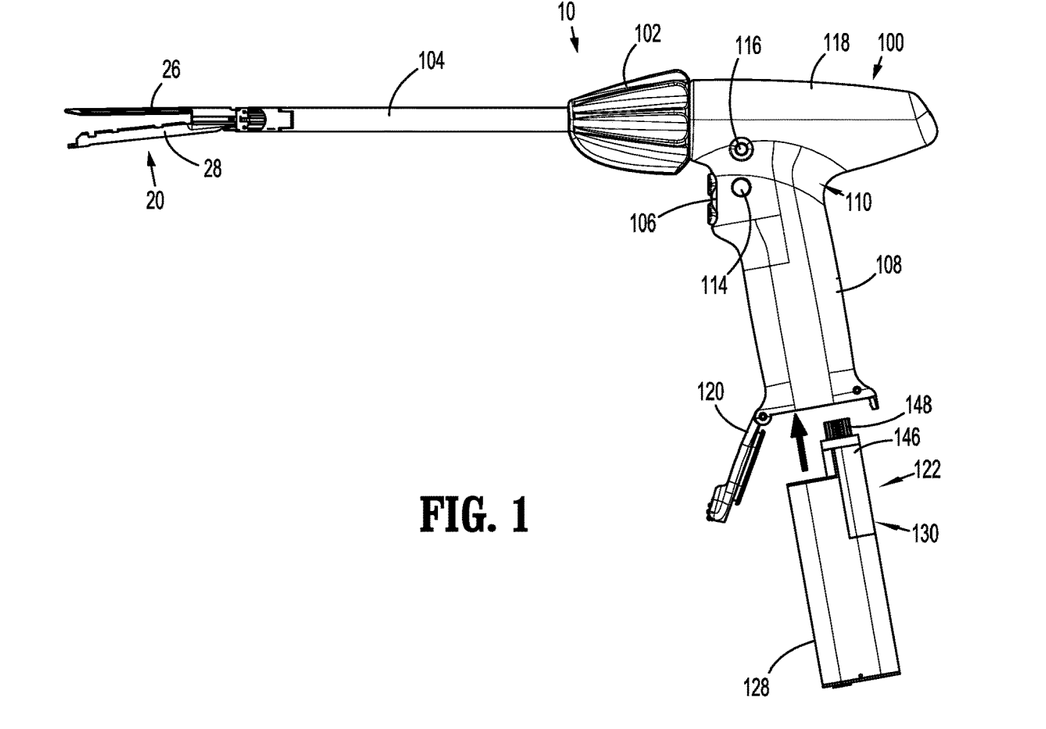
FIG. 1 is a side view illustrating a hand-held electromechanical surgical instrument including a handle assembly, with a surgical instrument module shown separated, a shaft portion coupled to the handle assembly, and a surgical end effector coupled to the shaft portion.
Figure 2:
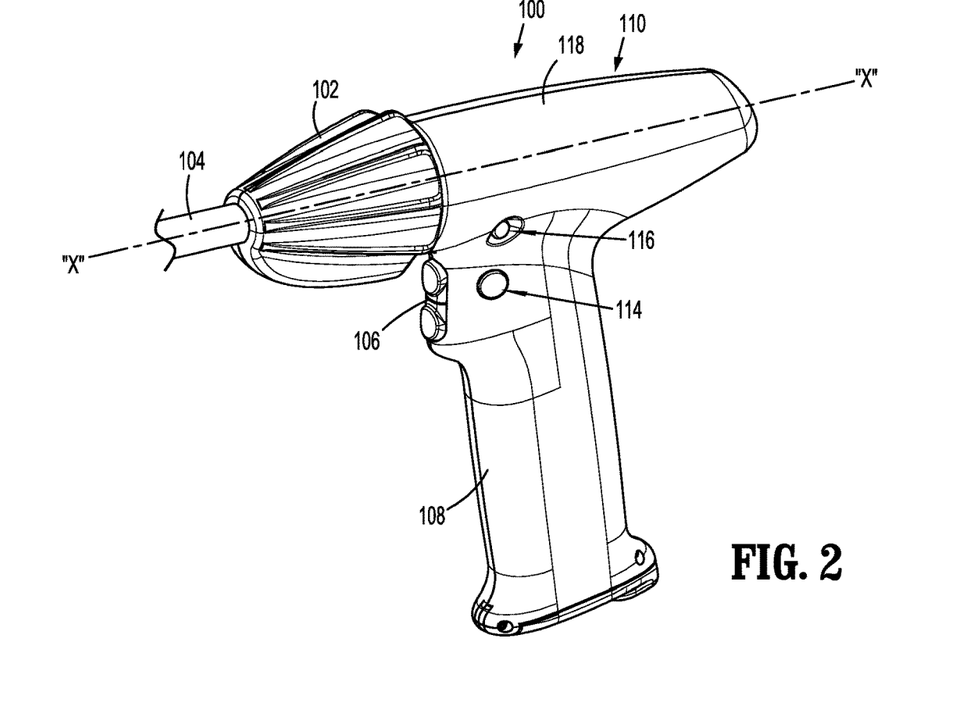
FIG. 2 is a partial perspective view illustrating a handle housing of the handle assembly of FIG. 1.

With reference to FIGS. 1 and 2, a surgical instrument, in accordance with an embodiment of the present disclosure, is generally designated as 10, and is in the form of a powered hand-held electromechanical linear stapler configured for selective coupling thereto of a surgical end effector 20. The end effector 20 is configured for actuation and manipulation by the linear stapler 10. The hand-held electromechanical surgical instrument 10 includes a handle assembly 100, a knob housing 102 coupled to the handle assembly 100, and a shaft portion 104 extending distally from the knob housing 102 and configured for selective connection with a surgical attachment, such as, for example, the end effector 20.

The handle assembly 100 includes a disposable and sterile handle housing 110 having a body, such as, for example, a barrel portion 118, a handle portion 108 extending perpendicularly downward from the barrel portion 118 or transversely and proximally from the barrel portion 118, and a hinged door 120 pivotably coupled to the handle portion 108. The door 120 is selectively opened and closed to allow for the insertion or removal of a non-sterile or sterile surgical instrument module 122. The handle portion 108 and the door 120 each have an inner periphery collectively defining a sterile barrier for the surgical instrument module 122 upon closing the door 120. In aspects, a proximal end portion or any suitable location of the barrel portion 118 may have a clear window (not shown) to allow for viewing of a display (e.g., an LCD, not shown).

The handle assembly 100 has a fire switch 106 configured and adapted to actuate the various functions of the end effector 20. The fire switch 106 may be constructed as a toggle bar pivotably coupled to the handle portion 108 of the handle housing 110. An activation of the fire switch 106 activates a motor 112 (FIGS. 3A and 3B) to advance or retract a firing rod (not explicitly shown) of the surgical instrument 10 depending on whether a top button or a bottom button of the fire switch 106 is actuated. The firing rod is coupled to a drive assembly (not explicitly shown) of the end effector 20 (which includes a knife rod and an actuation sled), such that advancement of the firing rod advances the drive assembly of the end effector 20, which closes jaw members 26, 28 of the end effector 20 and fires the end effector 20 when a safety switch 116 is in an actuated state.

The handle assembly 100 has an articulation switch 114 extending transversely through the handle portion 108 and protruding outwardly from left and right sides of the handle portion 108. The articulation switch 114 is configured to actuate an articulation of the end effector 20 (e.g., move the end effector 20 along a horizontal plane between a position coaxial with the shaft portion 104 and multiple positions out of alignment with the shaft portion 104). The knob housing 102 is rotatably coupled to the handle housing 110 and has the shaft portion 104 non-rotationally coupled thereto. As such, a manual rotation of the knob housing 102 results in a corresponding rotation of the end effector 20 (e.g., the end effector 20 rotates about a central longitudinal axis "X" defined by the shaft portion 104).

With reference to FIGS. 1, 3A, 3B, and 4, the surgical instrument module 122 of the handle assembly 100 includes a sterile outer shell 128 and a reusable power assembly 130 configured for removably receipt in the outer shell 128. The outer shell 128 has a cover 132 received in an open bottom end of the outer shell 128, and a spring-loaded pull tab 134 to facilitate removal of the cover 132.

Figures 3A, 3B, 4:
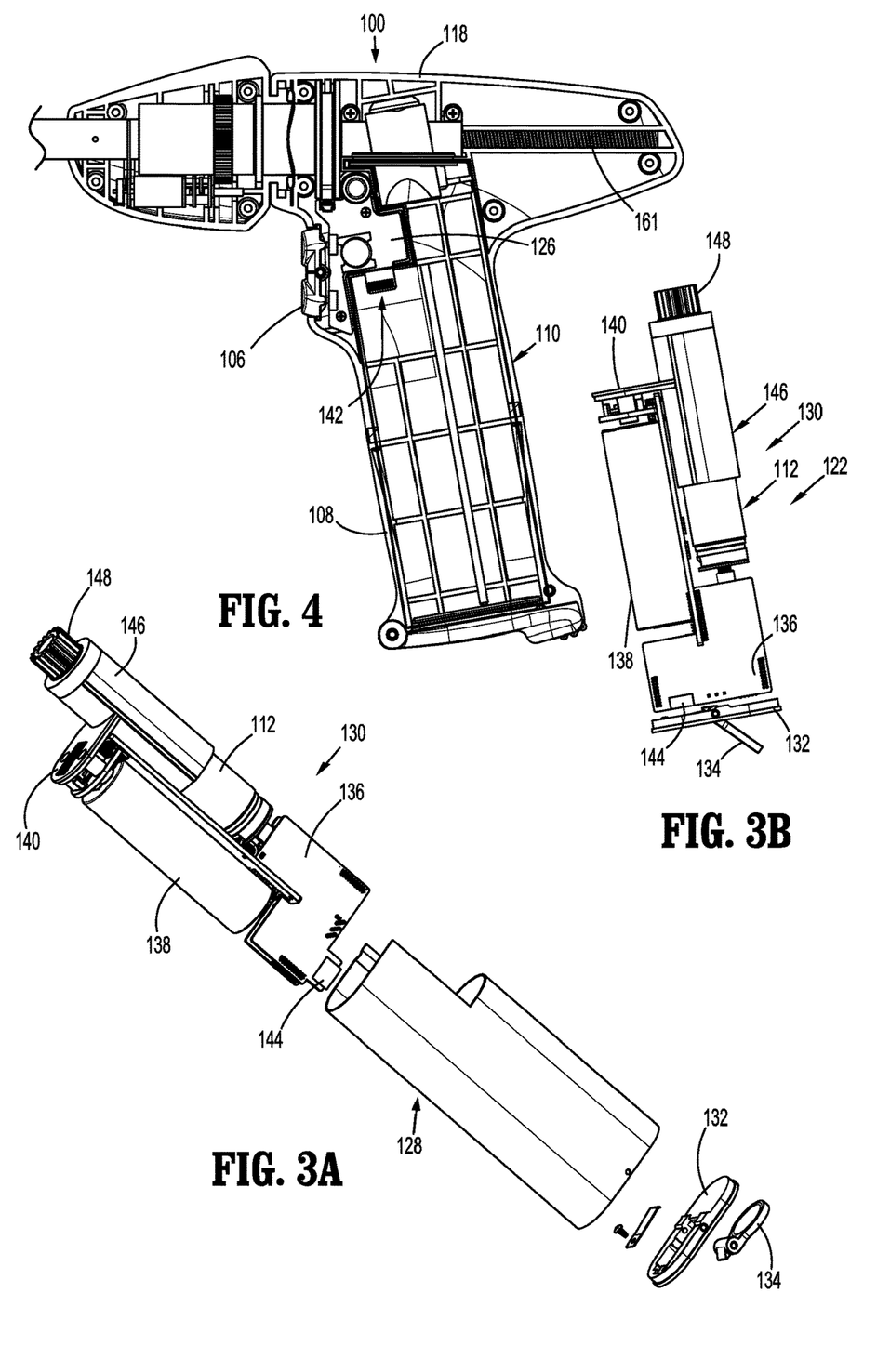
FIG. 3A is a perspective view, with parts separated, illustrating the surgical instrument module of FIG. 2 including a power assembly and an outer shell.
FIG. 3B is an assembled front view illustrating the power assembly of the instrument module of FIG. 3A.
FIG. 4 is a side view, with a housing half of the handle housing removed, illustrating internal components of the handle assembly.

The power assembly 130 of the instrument module 122 includes the motor 112, such as, for example, an electrical drive motor, which is electrically connected or wirelessly connected to a printed circuit board 136 and a battery 138. In aspects, the battery 138 may include a boost circuit and may be rechargeable (e.g., wirelessly). The battery 138 has a card edge connector 140 configured for detachable receipt of a card edge header 142 of the handle assembly 100 to allow for communication from the fire switch 106, the safety switch 116, the articulation switch 114, and an articulation encoder to the battery 138. The printed circuit board 136 may include a USB charging connector 144 to allow for the battery 138 to be recharged with a USB charger or wirelessly (e.g., via induction). In aspects, the printed circuit board 136 may have a motor controller or a processor.

Figure 5:
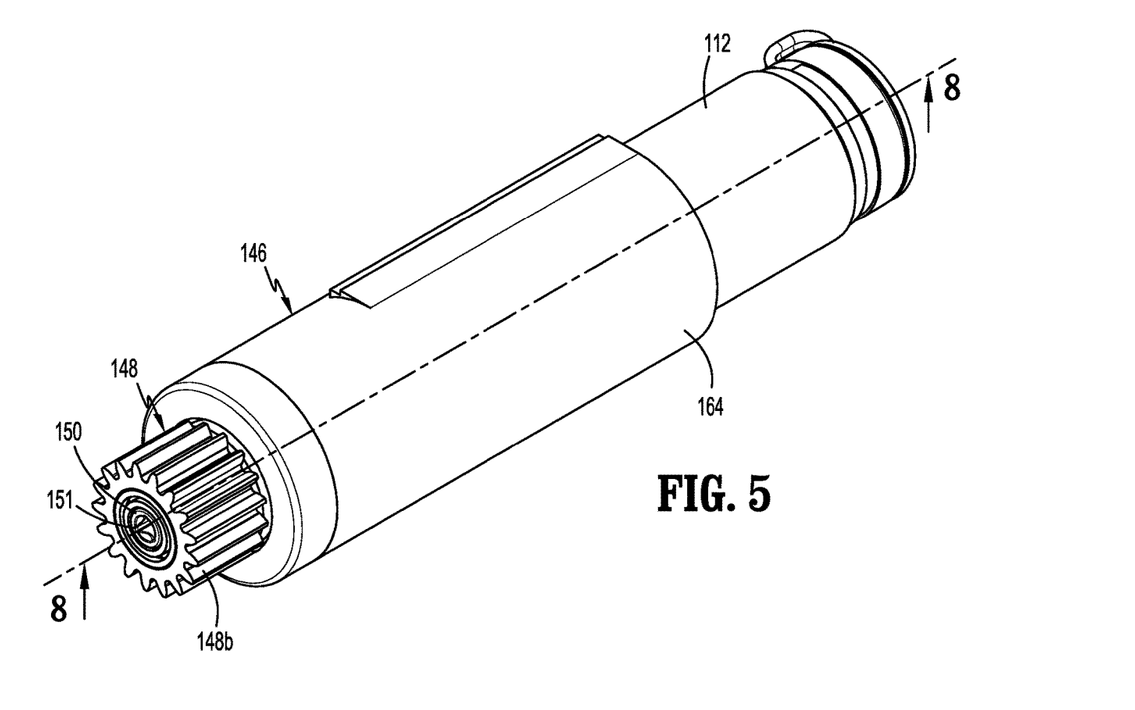
FIG. 5 is a perspective view illustrating a motor, an elongate ring gear, and outputs of the instrument module of FIG. 3A.
Figure 6:
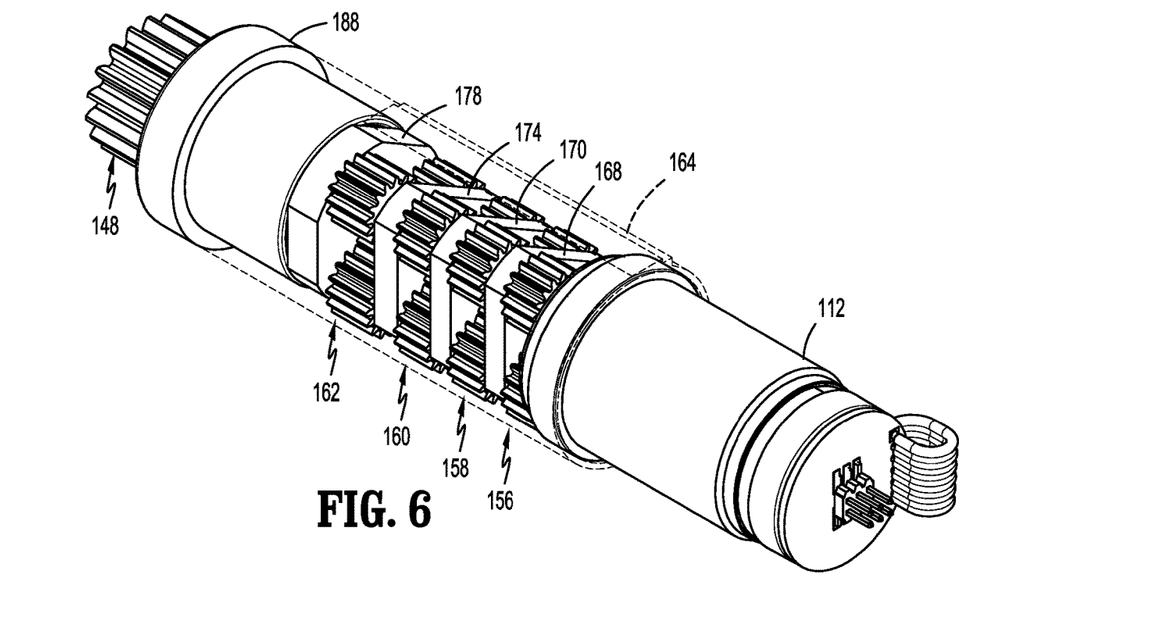
FIG. 6 is a perspective view, with the elongate ring gear shown in phantom, illustrating a plurality of planetary gear assemblies of the instrument module of FIG. 3A.
Figure 7:
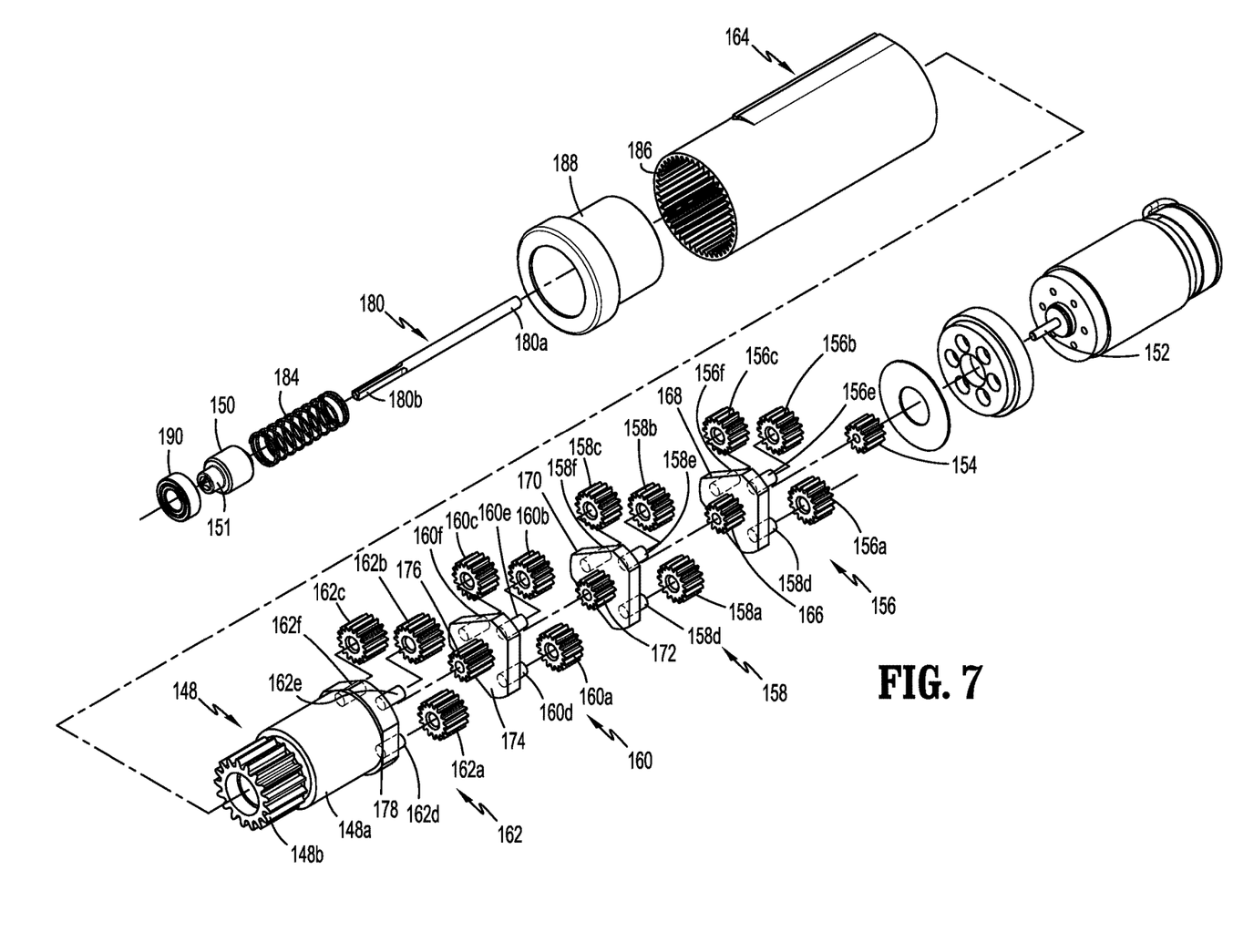
FIG. 7 is a perspective view, with parts separated, of the components shown in FIG. 5.
Figure 8:
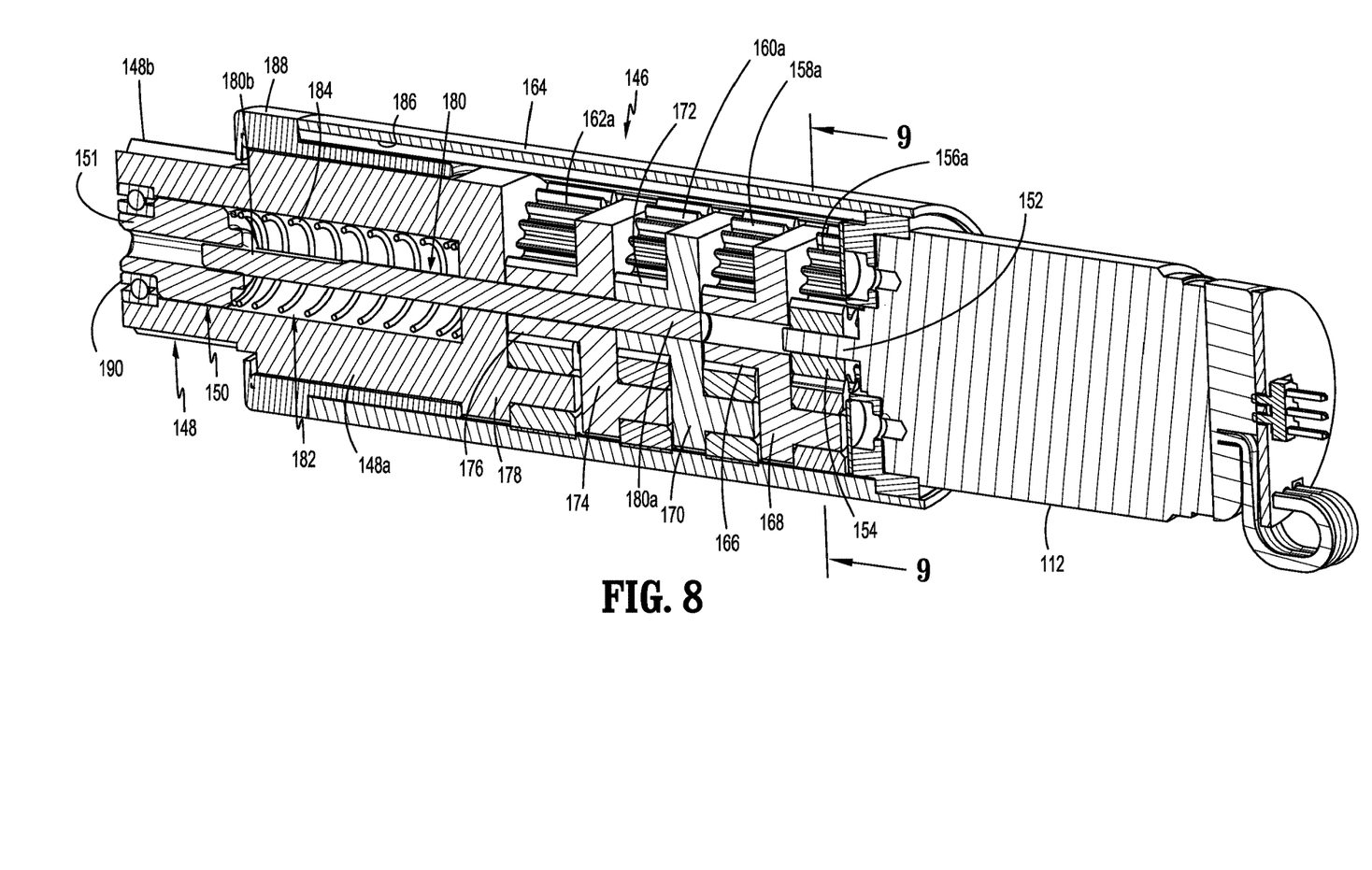
FIG. 8 is a cross-sectional view taken along line 8-8 in FIG. 5.
Figure 9:
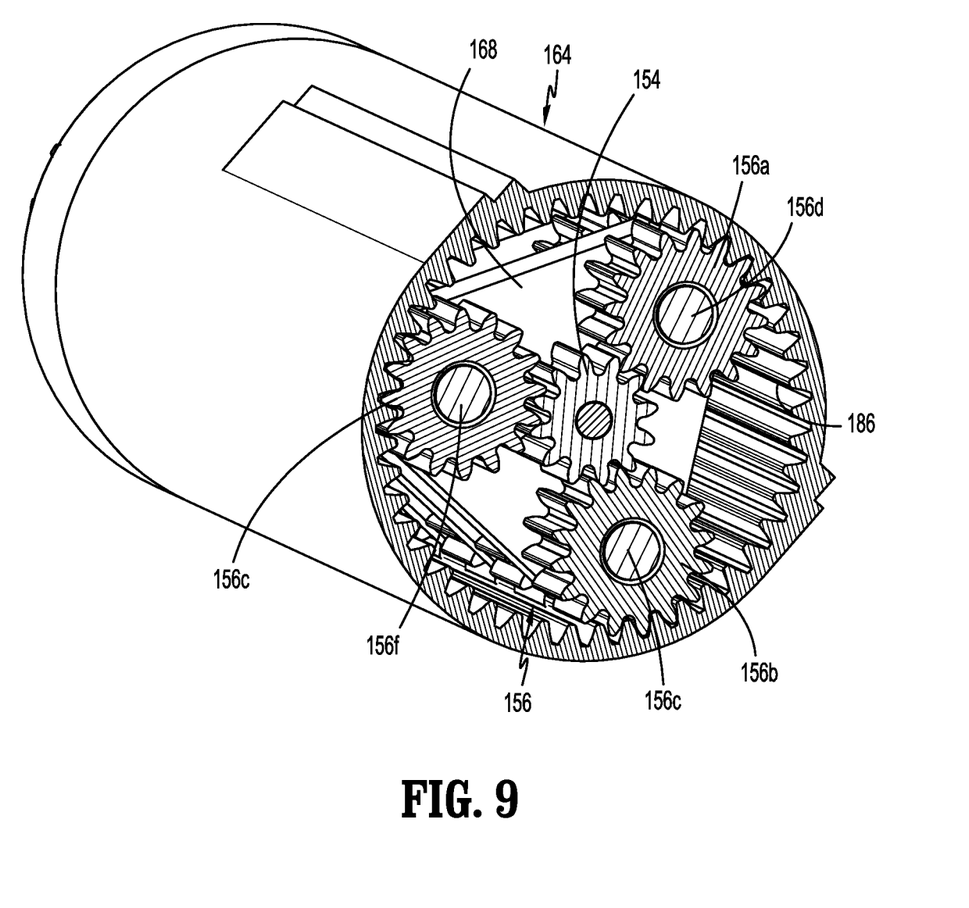
FIG. 9 is a cross-sectional view taken along line 9-9 in FIG. 8.

The instrument module 122 further includes a gearbox 146, such as, for example, a planetary gearbox, operably coupled to the drive motor 112, and first and second outputs 148, 150 (FIG. 5) drivingly coupled to the gearbox 146 and configured to rotate about a longitudinal axis defined by the gearbox 146. The gear box 146 is configured to transfer power from the motor 112 into a rotation of the first output 148 at a high-torque and low-speed, and a rotation of the second output 150 at a high-speed and low-torque. Rotation of the outputs 148, 150 by the motor 112 functions to drive shafts and/or gear components of the handle assembly 100 in order to perform the various operations of the end effector 20. For example, the motor 112 is configured to move the jaw members 26, 28 of the end effector 20 relative to one another and to fire staples from the end effector 20.

For a more detailed description of the various components responsible for transferring rotation of the outputs 148, 150 into movement of components of the end effector 20, reference may be made to U.S. Provisional Application No. 62/944,400, filed on Dec. 6, 2019, the entire contents of which are incorporated by reference herein.

With reference to FIGS. 5-9, further details of the various components of the instrument module 122 will now be described. The motor 112 has a rotatable motor shaft 152 (FIG. 7) to which a main sun gear 154 is non-rotatably fixed such that the main sun gear 154 rotates with the motor shaft 152 about a longitudinal axis defined by the motor shaft 152. The gear box 146 includes a plurality of planetary gear assemblies 156, 158, 160, 162 and an elongate ring gear 164 disposed about and operably coupled to the plurality of planetary gear assemblies 156, 158, 160, 162.

The first planetary gear assembly 156 is operably coupled to the main sun gear 154 such that the first planetary gear assembly 156 rotates about the longitudinal axis of the motor shaft 152 in response to a rotation of the main sun gear 154. The first planetary gear assembly 156 increases the torque output of the motor 112 while reducing the output rotational speed. The first planetary gear assembly 156 includes a first carrier 168, a first sun gear 166, and a plurality of planetary gears 156a, 156b, 156c. The first carrier 168 has a plurality (e.g., three) of pins 156d, 156e, 156f fixed thereto and extending proximally from a proximal side thereof. The first sun gear 166 is rotationally fixed to a distal side of the first carrier 168 and centrally aligned with the longitudinal axis of the motor shaft 152. The planetary gears 156a, 156b, 156c are rotatably coupled to the respective pins 156d, 156e, 156f of the first carrier 168. The planetary gears 156a, 156b, 156c are in meshing engagement with the main sun gear 154 to rotate in response to a rotation of the main sun gear 154. As will be described, the elongate ring gear 164 is rotationally fixed relative to the outer shell 128 (FIG. 3A) such that the first planetary gear assembly 156 rotates as a unit about the longitudinally axis of the motor shaft 152 in response to a rotation of the main sun gear 154.

The second planetary gear assembly 158 includes a second carrier 170, a second sun gear 172, and a plurality of planetary gears 158a, 158b, 158c. The second planetary gear assembly 158 has an increased torque output and reduced rotational speed output relative to the first planetary gear assembly 156. The second carrier 170 has a plurality (e.g., three) of pins 158d, 158e, 158f fixed thereto and extending proximally from a proximal side thereof. The second sun gear 172 is rotationally fixed to a distal side of the second carrier 170 and centrally aligned with the longitudinal axis of the motor shaft 152. The planetary gears 158a, 158b, 158c of the second planetary gear assembly 158 are rotatably coupled to the respective pins 158d, 158e, 158f of the second carrier 170. The planetary gears 158a, 158b, 158c are in meshing engagement with the first sun gear 166 of the first planetary gear assembly 156 and the fixed elongate ring gear 164 such that the second planetary gear assembly 158 rotates in response to a rotation of the first planetary gear assembly 156.

The third planetary gear assembly 160 includes a third carrier 174, a third sun gear 176, and a plurality of planetary gears 160a, 160b, 160c. The third planetary gear assembly 160 has an increased torque output and reduced rotational speed output relative to the second planetary gear assembly 158. The third carrier 174 has a plurality (e.g., three) of pins 160d, 160e, 160f fixed thereto and extending proximally from a proximal side thereof. The third sun gear 176 is rotationally fixed to a distal side of the third carrier 174 and centrally aligned with the longitudinal axis of the motor shaft 152. The planetary gears 160a, 160b, 160c of the third planetary gear assembly 160 are rotatably coupled to the respective pins 160d, 160e, 160f of the third carrier 174. The planetary gears 160a, 160b, 160c of the third planetary gear assembly 160 are in meshing engagement with the second sun gear 172 of the second planetary gear assembly 158 and the elongate ring gear 164 such that the third planetary gear assembly 160 rotates as a unit in response to a rotation of the second planetary gear assembly 158.

The fourth planetary gear assembly 162 includes a fourth carrier 178 and a plurality of planetary gears 162a, 162b, 162c. The fourth planetary gear assembly 162 has an increased torque output and reduced rotational speed output relative to the third planetary gear assembly 160. The fourth carrier 178 is connected to, monolithically formed with, or otherwise non-rotatably coupled to a proximal end of the first output 148 and has a plurality (e.g., three) of pins 162d, 162e, 162f fixed thereto and extending proximally from a proximal side thereof. The planetary gears 162a, 162b, 162c of the fourth planetary gear assembly 162 are rotatably coupled to the respective pins 162d, 162e, 162f of the fourth carrier 178. The planetary gears 162a, 162b, 162c of the fourth planetary gear assembly 162 are in meshing engagement with the third sun gear 176 of the third planetary gear assembly 160 and the elongate ring gear 164 such that the fourth planetary gear assembly 162 and the first output 148 rotate together in response to a rotation of the third planetary gear assembly 160. It is contemplated that the gear box 146 may include more or less than the four planetary gear assemblies and/or other types of gears.

Figure 10:
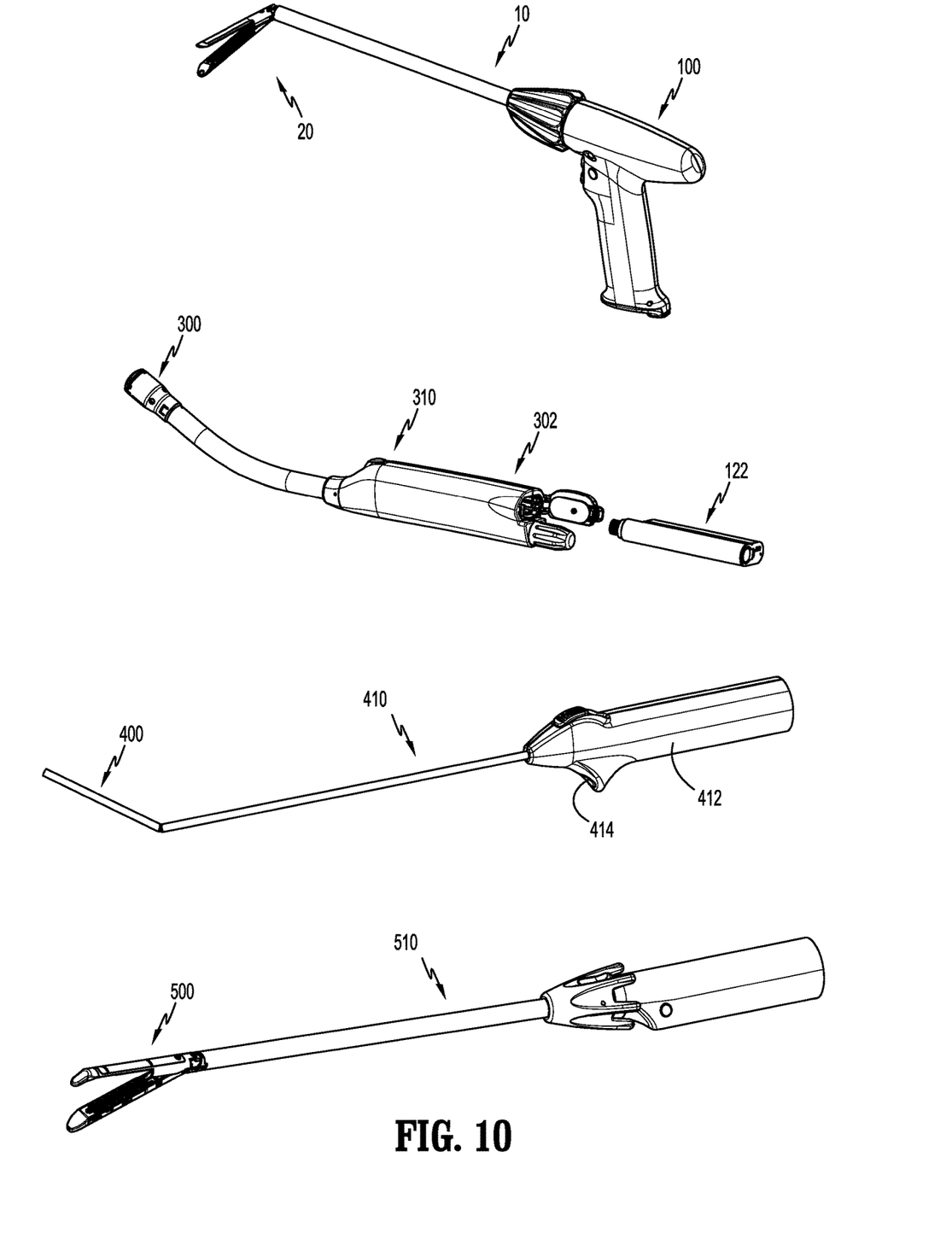
FIG. 10 illustrates four discrete surgical instruments all operable with the instrument module of FIGS. 3A-3B.

With continued reference to FIGS. 5-9, the first output 148 is configured to generate a relatively high torque (e.g., about 625 oz-in) and a relatively low speed (e.g., 24 rpm) and includes a cylindrical body 148a received in a distal end portion of the elongate ring gear 164, and a gear 148b, such as, for example, a pinion gear formed with a distal end portion of the cylindrical body 148a. The pinion gear 148b of the first output 148 is configured to be selectively operably coupled to a driven member (not explicitly shown) of a first type of surgical end effector, such as, for example, surgical end effector 20 (FIGS. 1 and 10) of the linear stapler 10 or a surgical end effector 300 (FIG. 10) of a circular stapler 310 (FIG. 10). It is contemplated that handle assemblies 100, 302 or other components of the surgical instruments 10, 310 have a corresponding driven component (e.g., a gear, rack, or the like) configured to selectively engage the pinion gear 148b upon receipt of the surgical instrument module 122 in the respective handle assembly 100, 302.

The surgical instrument module 122 further includes a drive shaft 180 having a proximal end portion 180a non-rotatably coupled to the second planetary gear assembly 158 such that the drive shaft 180 is configured to rotate with the second planetary gear assembly 158. In particular, the proximal end portion 180a of the drive shaft 180 is received within and rotationally fixed to the second sun gear 172 of the second planetary gear assembly 158. The drive shaft 180 has a distal end portion 180b extending longitudinally through the third and fourth planetary gear assemblies 160, 162 while being freely rotatable therein. The distal end portion 180b of the drive shaft 180 may have a non-circular cross-sectional shape, such as, for example, a tri-lobe shape.

The second output 150 is attached to the distal end portion 180b of the drive shaft 180 and is configured to rotate with the drive shaft 180 about a longitudinal axis of the drive shaft 180. The second output 150 is configured to generate a relatively low torque (e.g., 25 oz-in) and a relatively high speed (e.g., 600 rpm) and includes a socket 151 that is configured to operably couple to a corresponding driven element (not explicitly shown) of a different type of surgical end effector than the first output 148. For example, the second output 150 of the surgical instrument module 122 may be configured to carry out functions of a surgical end effector 400 (FIG. 10) of a hernia tacker 410 or a surgical end effector 510 (FIG. 10) of a small-diameter vascular stapler 500 (FIG. 10). It is contemplated that the handle assemblies or other components of the surgical instruments 410, 510 have a corresponding driven component (e.g., a rod) configured to selectively engage the socket 151 upon receipt of the surgical instrument module 122 in the respective handle housing.

The second output 150 is concentrically disposed within the first output 148 and is configured to rotate simultaneously with the first output 148 in response to an activation of the same motor, namely the motor 112. However, as noted above, the first and second outputs 148, 150 rotate at different speeds and with different torques from one another. The second output 150 is received in an elongate cavity 182 defined in the cylindrical body 148a of the first output 148. A biasing member 184 is disposed within the cavity 182 and captured between the second output 150 and an inner surface of the cylindrical body 148a of the first output 148. The biasing member 184 is configured to distally-bias the second output 150 into a position in which the second output 150 is concentric within the first output 148. The biasing member 184 ensures that even if the socket 151 of the second output 150 is out of radial alignment with the driven element of the end effector assembly that the socket 151 will engage the driven element as the second output 150 rotates the socket 151 into radial alignment with the driven element.

With continued reference to FIGS. 5-9, the elongate ring gear 164 of the gear box 146 encapsulates each of the planetary gear assemblies 156, 158, 160, 162 and is rotationally fixed relative to the outer shell 128 (FIG. 3A) and the motor 112. The elongate ring gear 164 has an annular inner surface defining a plurality of longitudinally-extending teeth 186 that are in meshing engagement with the planetary gears of each of the planetary gear assemblies 156, 158, 160, 162. A first bushing 188 may be provided to capture the first output 148 in the elongate ring gear 164 and a second bushing 190 may be provided to capture the second output 150 in the first output 148.

In operation, a surgical instrument is selected that is suitable for an operation to be performed. For example, the linear stapler 10 (FIG. 10) may be selected. The linear stapler 10 is typically used for stapling a type of tissue that is more suitable to receiving staples that are deployed with a high torque and at a low speed. The surgical instrument module 122 is inserted into the handle housing 110 of the linear stapler 10, whereby the pinion gear 148b of the first output 148 operably engages a driven element, such as a rack 161 (FIG. 4) or a corresponding pinion gear of the handle assembly 100 of the linear stapler 10. In aspects, a sterile, funnel-shaped insertion guide may be implemented to assist in passing the surgical instrument module 122 into the handle housing 110. When the insertion guide is removed, the handle housing 110 remains sterile through this aseptic transfer procedure.

With the instrument module 122 disposed within the handle housing 110, the door 120 is closed, thereby sealing the instrument module 122 in the sterile handle portion 108. Further, the card edge header 142 of the printed circuit board 126 of the handle assembly 100 is connected to the card edge connector 140 of the instrument module 130.

To operate the surgical end effector 20 of the linear stapler 10, the fire switch 106 (FIG. 1) may be toggled, whereby the battery 138 of the instrument module 122 provides power to the motor 112, which drives a rotation, in turn, of the first, second, third, and fourth planetary gear assemblies 156, 158, 160, 162. The planetary gear assemblies 156, 158, 160, 162 consecutively enhance the torque and reduce the speed output by the pinion gear 148b of the first output 148 compared to the torque and speed originating from the motor 112. The high-torque, low-speed output by the first output 148 results in the advancement of staples from the end effector 20 into tissue with a high force and at a low speed.

If a different surgical procedure is to be performed, for example, a hernia repair procedure, the hernia tacker 410 (FIG. 10) may be selected for use rather than the linear stapler 10. To properly treat tissue, the hernia tacker 410 demands less torque but a higher actuation speed than the linear stapler 10. The instrument module 122 is inserted into a handle portion 412 of the hernia tacker 410, whereby the socket 151 of the second output 150 engages a driven element (e.g., a rod) of the hernia tacker 410.

To operate the surgical end effector 400 of the hernia tacker 410, a fire switch 414 of the hernia tacker 410 may be toggled, whereby the battery 138 of the instrument module 122 provides power to the motor 112, which drives a rotation, in turn, of the first and second planetary gear assemblies 156, 158. Since the drive shaft 180 is fixed to the second sun gear 172 of the second planetary gear assembly 158, the drive shaft 180 rotates with the rotation of the second planetary gear assembly 158. The second output 150, which is non-rotatably attached to the distal end portion 180b of the drive shaft 180, rotates with the drive shaft 180 to effect a function of the hernia tacker 410, such as a deployment of a surgical tack into tissue at a low torque and a high speed.

It is contemplated that each of the first and second drive outputs 148, 150 may be simultaneously coupled to two distinct driven elements of a particular surgical instrument to perform discrete functions of the surgical instrument.

Any of the components described herein may be fabricated from either metals, plastics, resins, composites or the like taking into consideration strength, durability, wearability, weight, resistance to corrosion, ease of manufacturing, cost of manufacturing, and the like. Any of the gears disclosed herein may be configured as any suitable gear, such as bevel gears, spur gears, spiral gears, worm gears, or the like.

It will be understood that various modifications may be made to the embodiments of the presently disclosed surgical instruments and surgical instrument modules. Therefore, the above description should not be construed as limiting, but merely as exemplifications of embodiments. Those skilled in the art will envision other modifications within the scope and spirit of the present disclosure.

The invention claimed is:

1. A surgical instrument module for powering surgical end effectors, the surgical instrument module comprising:
    a motor having a rotatable motor shaft defining a longitudinal axis;
    a main sun gear fixed to the motor shaft and configured to rotate with the motor shaft;
    a first planetary gear assembly operably coupled to the main sun gear such that the first planetary gear assembly rotates about the longitudinal axis in response to a rotation of the main sun gear;
    a second planetary gear assembly operably coupled to the first planetary gear assembly such that the second planetary gear assembly rotates in response to the rotation of the first planetary gear assembly;
    a drive shaft non-rotatably coupled to the second planetary gear assembly such that the drive shaft rotates with the second planetary gear assembly;
    a third planetary gear assembly operably coupled to the second planetary gear assembly such that the third planetary gear assembly rotates in response to the rotation of the second planetary gear assembly;
    a fourth planetary gear assembly operably coupled to the third planetary gear assembly such that the fourth planetary gear assembly rotates in response to the rotation of the third planetary gear assembly;
    a high-torque output configured to be operably coupled to a driven member of a first surgical end effector, the high-torque output being non-rotatably coupled to the fourth planetary gear assembly such that the high-torque output rotates with the fourth planetary gear assembly; and
    a high-speed output configured to be operably coupled to a driven member of a second surgical end effector, the high-speed output being non-rotatably coupled to the drive shaft such that the high-speed output rotates with the drive shaft.

2. The surgical instrument module according to claim 1, wherein the high-speed output is concentrically disposed within the high-torque output.

3. The surgical instrument module according to claim 2, wherein the high-speed and high-torque outputs are configured to rotate simultaneously in response to an activation of the motor.

4. The surgical instrument module according to claim 1, wherein the high-torque output includes a pinion gear and the high-speed output includes a socket.

5. The surgical instrument module according to claim 1, wherein the drive shaft extends longitudinally through the third and fourth planetary gear assemblies.

6. The surgical instrument module according to claim 5, wherein the drive shaft has a proximal end portion fixed to the second planetary gear assembly, and a distal end portion disposed within and rotatable relative to the high-torque output.

7. The surgical instrument module according to claim 1, wherein the high-torque output defines a cavity therein, and the high-speed output is received in the cavity.

8. The surgical instrument module according to claim 7, wherein the high-speed output is configured to move longitudinally relative to and along the drive shaft.

9. The surgical instrument module according to claim 8, further comprising a biasing member captured between the high-speed output and an inner surface of the high-torque output, wherein the biasing member is configured to distally-bias the high-speed output.

10. The surgical instrument module according to claim 1, further comprising an elongate ring gear in meshing engagement with each of the planetary gear assemblies.

11. The surgical instrument module according to claim 10, wherein each of the planetary gear assemblies is disposed within the elongate ring gear.

12. The surgical instrument module according to claim 10, wherein the elongate ring gear is rotationally fixed relative to the motor.

13. The surgical instrument module according to claim 1, wherein the first planetary gear assembly includes:
    a first carrier;
    a plurality of planetary gears rotatably coupled to the first carrier and operably engaged with the main sun gear; and
    a first sun gear rotationally fixed to the first carrier.

14. The surgical instrument module according to claim 13, wherein the second planetary gear assembly includes:
    a second carrier;
    a plurality of planetary gears rotatably coupled to the second carrier and operably engaged with the first sun gear; and
    a second sun gear rotationally fixed to the second carrier.

15. The surgical instrument module according to claim 14, wherein the drive shaft has a proximal end portion disposed within and rotationally fixed to the second sun gear.

16. The surgical instrument module according to claim 14, wherein the third planetary gear assembly includes:
    a third carrier;
    a plurality of planetary gears rotatably coupled to the third carrier and operably engaged with the second sun gear; and
    a third sun gear rotationally fixed to the third carrier.

17. The surgical instrument module according to claim 16, wherein the fourth planetary gear assembly includes:
    a fourth carrier non-rotationally fixed to the high-torque output; and
    a plurality of planetary gears rotatably coupled to the fourth carrier and operably engaged with the third sun gear.

18. The surgical instrument module according to claim 17, further comprising an elongate ring gear in meshing engagement with the plurality of planetary gears of each of the planetary gear assemblies.

19. The surgical instrument module according to claim 18, further comprising an outer shell in which the elongate ring gear is received, wherein the elongate ring gear is non-rotatable relative to the outer shell.

20. The surgical instrument module according to claim 19, further comprising:
    a battery received in the outer shell and configured to power the motor; and
    a printed circuit board received in the outer shell and in communication with the battery and the motor.

* * * * *